United States Patent [19]
Chu

[11] Patent Number: 5,541,059
[45] Date of Patent: Jul. 30, 1996

[54] IMMUNOASSAY DEVICE HAVING AN INTERNAL CONTROL OF PROTEIN A AND METHODS OF USING SAME

[76] Inventor: Albert E. Chu, 140 Roblar Ave., Hillsborough, Calif. 94010

[21] Appl. No.: 176,277

[22] Filed: Dec. 29, 1993

[51] Int. Cl.⁶ .................. G01N 33/543; G01N 33/553; G01N 33/569
[52] U.S. Cl. .................. 435/5; 422/56; 422/57; 422/58; 422/61; 435/7.2; 435/7.32; 435/7.34; 435/7.9; 435/7.92; 435/7.93; 435/7.94; 435/805; 435/810; 435/967; 435/973; 435/287.2; 436/512; 436/513; 436/518; 436/525; 436/531; 436/534; 436/169; 436/810
[58] Field of Search .................. 422/56–58, 61; 435/5, 7.2, 7.21, 7.32, 7.34, 7.9, 7.92, 7.93, 7.94, 287, 291, 805, 810, 970, 973, 967; 436/512, 513, 518, 524, 525, 527, 528, 531, 533, 534, 169, 805, 807, 810

[56] References Cited

U.S. PATENT DOCUMENTS

| | | | |
|---|---|---|---|
| 3,966,898 | 6/1976 | Sjöquist et al. | 424/12 |
| 4,169,138 | 9/1979 | Jonsson | 424/12 |
| 4,292,403 | 9/1981 | Duermeyer | 436/513 |
| 4,632,901 | 12/1986 | Valkirs et al. | 435/5 |
| 4,806,311 | 2/1989 | Greenquist | 422/56 |
| 4,853,335 | 8/1989 | Olsen et al. | 436/525 |
| 5,006,464 | 4/1991 | Chu et al. | 422/58 |
| 5,008,080 | 4/1991 | Brown, III et al. | 422/56 |
| 5,026,653 | 6/1991 | Lee et al. | 436/518 |
| 5,132,085 | 7/1992 | Pelanek | 422/55 |
| 5,356,785 | 10/1994 | McMahon et al. | 435/7.92 |

FOREIGN PATENT DOCUMENTS 0200381  11/1986  European Pat. Off.

OTHER PUBLICATIONS

Product information literature: "GammaBind™ G. Engineered Protein G", (1987), Genex Corporation.
Björck et al, "Purification & Some Properties of Streptococcal Protein G, A Novel IgG–Binding Reagent", *Journal of Immunology*, 1984, vol. 133(2), pp. 969–974.
Tijssen, *Practice & Theory of Enzyme Immunoassays*, 1985, vol. 15, Elsevier, pp. 31–32.

Primary Examiner—James C. Housel
Assistant Examiner—Christopher L. Chin
Attorney, Agent, or Firm—Flehr, Hohbach, Test, Albritton & Herbert

[57] ABSTRACT

Immunoassay devices and methods that employ non-antibody control substances are disclosed. A non-antibody substance, such as Protein A, that specifically binds to the Fc portion of IgG is used to determine whether patient sample is properly added to the device during the assay procedure.

33 Claims, 1 Drawing Sheet

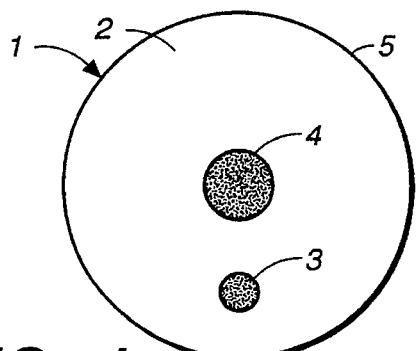
FIG._1
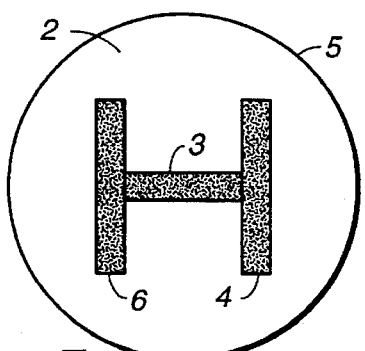
FIG._5
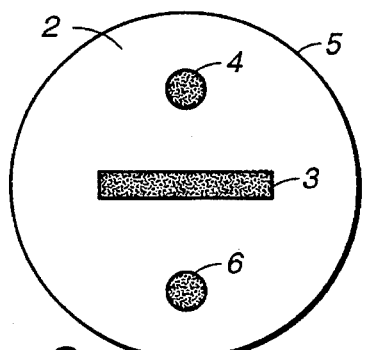
FIG._2
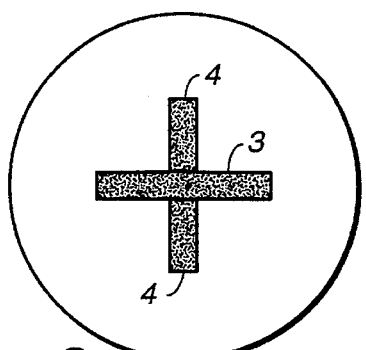
FIG._6
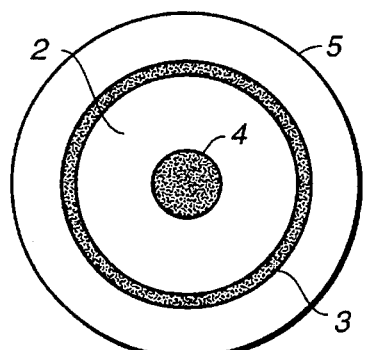
FIG._3
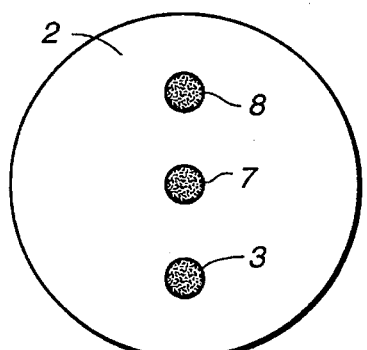
FIG._7
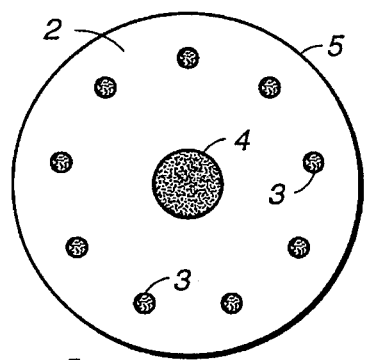
FIG._4

IMMUNOASSAY DEVICE HAVING AN INTERNAL CONTROL OF PROTEIN A AND METHODS OF USING SAME

BACKGROUND OF THE INVENTION

The technical field of this invention concerns internal controls for immunoassay devices and methods for the detection of an analyte in a liquid sample. More particularly, the present invention relates to the use of non-antibody control substances, such as Protein A, which are capable of binding to the Fc fragment of immunoglobulin. These substances serve as internal controls in such assay devices and methods, to ensure that reagents used in the assay are functioning and that the assay is performed properly.

Typically in an immunoassay for the detection of an antibody specific to an antigen (hereinafter referred to as "analyte antibody"), such as a test for the detection of antibodies to human immunodeficiency virus (HIV) or hepatitis C virus (HCV) antigen, a sample suspected of containing the analyte antibody is added to an immunoassay device surface having the particular antigen immobilized thereon. After the sample is added, an antibody specific to human antibody which has been labeled with an enzyme, a metal colloid, or some other marker, is added. If analyte antibody from the patient sample has bound to the antigen, the labeled antibody will also bind, thus indicating a positive test result.

Because immunoassays are often performed by laboratory personnel, human error is possible. Therefore, it is necessary to have controls to ensure that the testing is performed properly. Also because the reagents used in these immunoassays can often be of limited stability, controls are necessary to ensure that the reagents are functioning properly. Typically, when testing for the presence of analyte antibody, the immunoassay device will have a built-in control of an antibody directed to human immunoglobulin G (IgG), IgM, IgE, or IgA. Thus when a patient sample (typically plasma or serum) is added to the immunoassay device, immunoglobulin will bind to the internal control regardless of whether there is analyte antibody present in the sample. When labeled antibody is added, presence of the label at both internal control and antigen locations indicates the presence of the analyte antibody in the tested sample. Presence of the label at the internal control but not at the antigen location, indicates a negative test result. If little or no label is present at the internal control, then there was an error in the assay procedure, or one or more of the reagents was non-functioning, or the sample was diluted beyond the sensitivity of the system to detect immunoglobulin.

In an immunoassay for the detection of a specific antigen in a patient sample (hereinafter referred to as "analyte antigen"), an internal control will typically comprise the same antigen as the antigen to be detected. When a patient sample is added to the immunoassay device, any analyte antigen within the sample will bind to the area on the immunoassay device that has capture antibody immobilized thereon that is specific to the analyte antigen. When labeled antibody specific to the analyte antigen is added, it will bind to any analyte antigen captured from the patient sample and it will bind to the antigen of the internal control. This controls for the proper addition and functioning of the labeled antibody, but does not control for the proper addition of sample because if sample were inadvertently omitted from the immunoassay procedure, the internal control would still be able to bind to the labeled-antibody.

Protein A from *Staphylococcus aureus* has the ability to bind to the C(H2) and C(H3) domains of the Fc region of immunoglobulins, particularly IgG. In addition to this dominant Fc interaction which is a pseudo-immuno (non-antibody type) reaction, Protein A binds with lower avidity to the Fab region of certain immunoglobulin classes. The type of interaction of Protein A with immunoglobulins has two main practical advantages: first, since the antigen-binding region of the antibody molecule is not involved, any antigen-antibody reaction is unaffected, and second, because Protein A reacts with immunoglobulin from several different species, it has wide applicability in immunoassays.

While Protein A has found wide application in immunochemistry and immunohistochemistry, it has heretofore not been used as an internal assay control in immunoassay devices. This is probably because researchers believe that the Fc portion of the IgG in the sample to be assayed would bind the Protein A control, leaving only the Fab portion of the IgG exposed. Because the Fab portion of IgG does not bind to Protein A, one would not expect the system to work as an internal control. Thus, Protein A, although inexpensive and widely available, has not previously been used as a control substance in immunoassays devices.

The use of Protein A in immunoassay devices is described in U.S. Pat. No. 4,169,138, incorporated herein by reference, which discloses a method for detecting analyte antibodies bound to an antigen wherein a sample suspected of containing analyte antibody is added to a surface having antigen coated thereon. Next, Protein A which is bound to small water-insoluble particles is added. The particle/Protein A complex binds to analyte antibody, if present, thus forming a visible coating if analyte antibody has bound to the antigen.

U.S. Pat. No. 3,966,898, incorporated herein by reference, describes methods for labeling Protein A. The labeled Protein A is then used to detect IgG bound to an antigen or hapten.

None of the foregoing references is believed to disclose the present invention as claimed and is not presumed to be prior art. The references are offered for the purpose of background information.

There is an ongoing need to reduce the costs of immunoassay devices while improving upon their sensitivity and reproducibility. The antibodies and/or antigens typically used for assay controls can often be costly because their production and purification is labor-intensive. Another drawback of using antibodies for controls is that their sensitivity can vary from lot to lot, thus they can require substantial quality control testing. It would be desirable to have an internal control that, like antibody to human IgG, has the capability of binding to antibodies in human serum, yet is inexpensive to manufacture, reproducible, and comes from a reliable source.

SUMMARY OF THE INVENTION

In view of the foregoing, it is an object of the present invention to provide an analytical device and methods for the detection of analyte antibody or analyte antigen in a sample, while providing a reliable and inexpensive internal control.

This and other objects and features of the invention will be apparent to those skilled in the art from the following detailed description and appended claims.

An analytical device and methods are described for use in immunoassays for the detection of analyte antibody or analyte antigen in a liquid sample suspected of containing such antibody or antigen. For the detection of analyte antibody, the device comprises antigen, for which the analyte antibody is specific, immobilized on an a first area of a solid phase; and a non-antibody control substance immobilized on a second area of a solid phase. The control substance is capable of binding to the Fc fragment of immunoglobulin. In a preferred embodiment, the solid phase of the device comprises 1) a membrane having an upper and lower surface, the upper surface having the areas of immobilized antigen and control substance; and 2) an absorbent body in liquid-transferring contact with the lower surface of the membrane, such that when a sample, such as human serum, is added to the upper surface of the membrane, analyte antibody in the sample, if present, will bind to the antigen and human IgG in the sample will bind to the control substance, while the remainder of the sample flows through the membrane and into the absorbent body.

For the detection of analyte antigen, the device comprises a capture antibody, specific for said antigen, immobilized on an a first area of a solid phase; and a non-antibody control substance immobilized on a second area of a solid phase.

One method aspect of the present invention allows one to determine whether functioning reagents have been added in proper sequence to an analytical device for the detection of analyte antibody. The method comprises the steps of 1) applying liquid sample suspected of containing analyte antibody to the first and second areas having immobilized thereon, respectively, antigen for which the analyte antibody is specific, and a non-antibody control substance; 2) adding a labeled non-antibody substance capable of binding to the Fc fragment of immunoglobulin; and 3) examining the first area for the presence of the labeled substance.

BRIEF DESCRIPTION OF THE DRAWINGS

FIG. 1 shows the membrane surface of an immunoassay device having a circular control substance area and a circular antigen area.

FIG. 2 shows the membrane surface of an immunoassay device having a bar-shaped control substance area and two separate antigen areas on either side of the control substance area.

FIG. 3 shows the membrane surface of an immunoassay device having a circular rim of control substance and an antigen area within the circular rim.

FIG. 4 shows the membrane surface of an immunoassay device having a dotted circular rim of control substance and an antigen area within the dotted circular rim.

FIG. 5 shows the membrane surface of an immunoassay device having a central horizontal bar of control substance and two vertical bars of a first and second antigen.

FIG. 6 shows the membrane surface of an immunoassay device having a horizontal bar of control substance and a vertical bar of antigen.

FIG. 7 shows the membrane surface of an immunoassay device having a central capture antibody area, an upper antigen area, and a lower control substance area.

DESCRIPTION OF THE PREFERRED EMBODIMENTS

The present invention comprises immunoassay devices and methods that employ non-antibody control substances. As used herein, the term "non-antibody control substance" refers to a protein or other molecule that is capable of specifically binding to the Fc fragment of IgG. The control substances are used in place of antibody to IgG or specific antigen as an internal control. In a preferred embodiment, the control substance is Protein A. In the following detailed description of the preferred embodiments, reference will be made to Protein A. However, it is to be understood that the present invention also encompasses the use of other non-antibody substances, native or recombinant, that are capable of binding to the Fc region of immunoglobulins. For example, Protein G, isolated from streptococcal bacteria, also binds to the constant region of many types of IgGs. It has been used to detect, quantify and purify IgG antibodies.

The present invention can be used in any immunoassay device format that utilizes an antigen immobilized on a solid-phase for the detection of analyte antibody in a sample. For example the solid-phase could be the wells of a 96-well microtiter plate, which are commonly used for immunoassays. Protein A can be coated to the surface of one or more of the wells, while antigen is coated onto the remainder of the wells. The present invention will also find use in a bead-type immunoassay format, which is commonly used in the art. In this format, assay control beads will be coated with Protein A whereas test beads will be coated with antigen.

One preferred embodiment of the invention employs membrane-based immunoassay devices. Membrane-based immunoassay devices typically comprise an absorbent body and a permeable membrane layer covering the upper surface of the absorbent body. Such devices are widely used in the diagnostic arts and are described, for example, in U.S. Pat. No. 5,006,464, incorporated herein by reference. As used herein the term "membrane" encompasses any material capable of immobilizing the antigen and Protein A employed in the practice of the present invention, and through which a liquid sample can pass. Such materials encompass but are not limited to fiberglass, nylon, nitrocellulose, and other natural or synthetic materials that can be coupled directly or indirectly to the selected antigen.

The absorbent body of the membrane-based embodiment of the present invention can employ any of the known and conventionally employed absorbent materials that serve to draw liquid through a porous membrane, such as, for example, by capillary action. Useful known materials include cellulose acetate fibers, polyester, polyolefin or other such materials. It has also been found convenient to use layers of commercially available filter paper that can be selected to provide sufficient volume to absorb the liquid employed during the assay of the present invention.

The membrane layer and absorbent body are usually encased in a housing that has an opening so that at least part of the membrane surface is exposed. The device may have additional components that improve the functioning of the device, for example, a component that improves the flow of the sample through the membrane. The membrane may be pre-treated using methods known in the art to prevent non-specific binding of sample or immunoassay reagents to the membrane surface.

In the membrane-based immunoassay device, antigen is applied to the membrane using techniques known in the art. As used herein, the term "antigen" refers to any substance capable of eliciting an immune response and includes, but is not limited to, Human Immunodeficiency Virus (HIV) antigens, Hepatitis virus antigens (HCV, HBV, HAV), *Toxoplasmosis gondii*, Cytomegalovirus, *Helicobacter pylori*, Rubella, and the like. The antigen can be applied to the membrane directly or coated onto microparticles which are then entrapped by the membrane. The antigen is applied only to a portion of the exposed membrane surface. Protein A is also applied to the membrane at a different area of the exposed membrane surface. The concentration of Protein A is not critical; generally 1 mg/ml is adequate. The remainder of the exposed surface area can be blocked with any solution that does not contain IgG and that prevents non-specific binding of the sample and the Protein A conjugate, for example, a solution of bovine serum albumin (BSA). After the antigen and Protein A control have been immobilized on the membrane, the immunoassay device can be packaged and stored until it is used for testing for analyte antibody.

In a typical non-competitive immunoassay, a sample, such as human plasma, serum, or treated whole blood suspected of containing analyte antibody is added to the entire surface of the exposed membrane so that the areas having immobilized antigen and Protein A are both covered by the sample. Analyte antibody, if present in the sample, will bind to the antigen. IgG present in the sample will bind to the Protein A control via its Fc region. Depending upon the nature of the sample and the type of membrane used, it may or may not be necessary to add a wash buffer to rinse extraneous sample through the membrane.

Next, a non-antibody substance capable of binding to the Fc region of immunoglobulins, such as Protein A, labeled with any marker that permits detection is added to the membrane. It is preferable to use non-antibody conjugates because antibody conjugates will bind to the Protein A control if the patient sample is inadvertently omitted; thus the proper addition of sample would not be controlled. The Protein A may be labeled with any of the conventional markers such as radioactive, enzyme, or metal complex markers which are conjugated to the Protein A.

Formation of conjugates between immunological substances and labels are well known, e.g., (a) radioactive labels—U.S. Pat. No. 3,646,346, Hunter et al., Nature 142 (1962), 945, (b) enzyme labels—U.S. Pat. Nos. 3,654,090, 3,791,931 and 3,817,838, Wilson et al., Immunofluorescence and Related Staining Techniques, Knapp., W. et al., Eds. L. Sevier-North Holland, Bio-Medical Press, New York-Amsterdam, 1978, pp. 215–224; (c) fluorescent quencher labels—U.S. Pat. No. 3,996,345; (d) radioactive labels—U.S. Pat. No. 4,062,733; (e) fluorescent or enzyme labels U.S. Pat. No. 4,067,959; (f) chemiluminescent labels—U.S. Pat. No. 4,104,029; (g) non-enzymatic catalyst label—U.S. Pat. No. 4,160,645; (h) enzyme pair labels—U.S. Pat. No. 4,233,402, chemically induced fluorescent labels—U.S. Pat. No. 4,720,450; and (i) enzyme non-ionic charge labels—U.S. Pat. No. 4,287,300; all incorporated herein by reference. In addition, the labels disclosed in U.S. Pat. No. 4,366,241, incorporated herein by reference, may be employed. U.S. Pat. No. 3,966,898, referenced above, describes various procedures for labeling Protein A.

In a preferred embodiment, Protein A is labeled with a colloidal metal, preferably colloidal gold. The use of colloidal gold labels is well-known. See, e.g., *Scanning Electron Microscopy*, 1981, II, pp. 9–31, "Immunocytochemistry" Eds. Polak, J. N., et al., Bristol, London, Boston (1982) pp. 82–112, and *Journal of Neuroscience Methods*, 7(1983), pp. 1–18. Colloidal gold particle markers are simple to use in comparison to other conventional markers because they can be detected visually and thus do not require the instruments that are necessary for the detection of other types of markers such as radioactive isotopes. Furthermore, unlike enzymes, colloidal gold particle markers do not require the additional step of adding substrate.

When labeled Protein A is added to the membrane of the immunoassay device, it will bind to the Fc regions of the IgG bound to the Protein A control and the Fc regions of the analyte antibody which is bound to the antigen. Without being limited to any particular mechanism, it is hypothesized that the antibodies bound at the area of the Protein A control still have Fc fragments available for further binding to Protein A due to IgG immunocomplexes. Thus rather than having all the Fc regions bound to the Protein A control with only Fab regions available for further binding, an immunocomplex will comprise one antibody, with its Fc region bound to the control, complexed with a second antibody that has its Fc region available for binding with the Protein A conjugate.

After performing the assay, if label is detected at both the areas of the antigen and the Protein A control then the sample contains analyte antibody and the test is positive. If label is detected at the Protein A control area, but not at the antigen area, then the test is negative. If little or no label is detected, then there was an error in performing the immunoassay procedure, or one or more of the reagents was defective, or the sample was diluted beyond the sensitivity of the system to detect IgG.

The present invention can also be used in a sandwich-type immunoassay format that utilizes a capture antibody immobilized on a solid-phase for the detection of analyte antigen in a sample. In this embodiment, a monoclonal capture antibody specific for one epitope of the analyte antigen is immobilized on one area of the solid phase, while Protein A is immobilized on a second area of the solid-phase. The analyte antigen is inoculated onto a third area of the solid phase. When a patient sample such as human serum is added to the device, analyte antigen, if present in the sample, will bind to the capture antibody and IgG in the sample will bind to the Protein A.

Next, a monoclonal antibody cocktail is added comprising a first labeled antibody specific for a second epitope of the analyte antigen and a second labeled antibody specific for IgG. The first labeled antibody will bind to any analyte antigen that has been captured indicating a positive test result, as well as the analyte antigen inoculated onto the third area of the solid phase. The analyte antigen inoculated onto the membrane serves as a control to test for the proper functioning of the first labeled antibody. Thus, this area should always indicate the presence of label if the assay was performed correctly and if the reagents were properly functioning. The second labeled antibody will bind to IgG that has been bound to the Protein A.

Rather than using a monoclonal antibody cocktail, the first and second labelled antibodies could be added sequentially after the addition of the sample. In still another format, the sample and the first labelled antibody can be premixed together then added to the solid phase simultaneously. Next, the second labelled antibody is added. Various other assay permutations will be readily apparent to those skilled in the art.

The first and second labeled antibodies are preferably labeled with a colloidal metal using methods known in the art and described in the above-cited references. The two antibodies are selected so as not to cross-react with each other. Therefore, if there is no analyte antigen in the sample, a negative test result will be indicated by no staining at the site of the capture antibody. Only the Protein A site will be stained because IgG in the sample will bind and be labeled by the anti-human IgG-colloidal metal conjugate. If sample is inadvertently omitted during the performance of the assay, there will be little or no label bound to the Protein A control because the concentration of IgG in the conjugate is much less compared to that of the sample. Thus improper assay procedure is controlled.

If only one labeled antibody specific for the analyte antigen is used, without using labelled antibody specific for human IgG, then there will not be sufficient staining at the Protein A site by the labeled antibody to serve as an internal control because the Protein A will have most of its Fc binding sites already bound to IgG from the sample. Thus in a sandwich-type immunoassay it is preferable to use a labeled antibody specific for human IgG in conjunction with the labeled antibody for the analyte antigen.

In order that the invention described herein may be more fully understood, the following examples and detailed description of the drawings are set forth. It should be understood that these examples and drawings are for illustrative purposes only and are not to be construed as limiting the scope of the invention in any manner.

EXAMPLE 1

Inoculation of Protein A Control onto Membrane of Immunoassay Device

Referring to FIG. 1, 0.5 µl of a 1 mg/ml Protein A solution in 20 mM phosphate buffered saline is inoculated on the membrane, 2, of an EY™ FASTCHEK™ device, 1, and dried for 10 minutes to 2 hours. The pH range of other diluents, if used, is preferably between 6 to 8.5. Once inoculated and dried onto the membrane, the hydrophobic Protein A will not wash off during the performance of the assay. The inoculated Protein A, 3, covers a circular area on the membrane surface. The position on the membrane where it is inoculated can be anywhere but preferably at the edge of the rim, 5, of the immunoassay device, as indicated in FIG. 1. This is because the central location of the membrane will contain the inoculated antigen, 4, such as HIV 1 and 2, or HCV.

Referring to FIG. 2, Protein A is inoculated onto the membrane, 2, of an EY™ FASTCHEK™ device, 1, using the same procedure as described above. However, in this embodiment, the inoculated Protein A, 3 forms a bar in the middle of the EY™ FASTCHEK™ device, 1. With this embodiment, two different antigens can be inoculated, one above the bar, 3, and one below the bar, 6. Using this type of device, one can test for the presence two different analyte antibodies in the same sample.

In another embodiment, as shown in FIG. 5, two different antigens can be inoculated in the shape of parallel bars, 4 and 6, with a bar of Protein A, 3, horizontally disposed between the antigen bars.

In another embodiment, Protein A can be inoculated so as to form an open circle, 3, (as shown in FIG. 3), or a dotted circle (as shown in FIG. 4) around the rim, 5, of the EY™ FASTCHEK™ device, 1.

These embodiments ensure that sample has been added to the entire surface of the membrane.

Referring to FIG. 6, Protein A can be inoculated in the form of a bar 3, and the antigen can be inoculated in the form of a second bar, 4, that intersects the center of the Protein A bar so as to form a plus sign. After performing the assay procedures, the presence of a red zone in the shape of a "−" sign indicates a negative test result, whereas a "+" sign indicates a positive test result.

EXAMPLE 2

Preparation of Colloidal Gold—Protein A Conjugate

The colloidal gold comprises a gold sol prepared in accordance with the procedure of Faulk, W. P., et al., Immunochem. 8:1081 (1981), incorporated herein by reference. Briefly summarized, 100 ml distilled water containing 0.01% chloro-auric acid solution is mixed with 4 ml of 1% trisodium citrate and boiled for 15 minutes. The solution turns from yellow to red at an optical density at 520 nm of about 1.

The Protein A/Colloidal gold conjugate can be prepared by mixing 100 ml of the colloidal gold solution with 100 ml of a 0.006 mg/ml solution of Protein A dissolved in water. The Protein A can be obtained commercially in lyophilized form, and dissolved directly into the water. Alternatively, the conjugate can be prepared in a more shelf-stable formulation in 1–3% BSA diluent with 0.05% $NaN_3$.

EXAMPLE 3

Assay for Antibody Detection

After inoculation of the Protein A and the antigen, as described in Example 1, the immunoassay device is used to test for the presence of analyte antibody in human serum or plasma. Two drops of 1% BSA or other blocking buffer are added to the surface of the membrane and allowed to absorb into the membrane. Next, one drop of human serum or plasma is allowed to absorb into the membrane. This is followed by the addition of two drops of Protein A—colloidal gold conjugate as prepared in Example 2.

After the labeled Protein A absorbs through the membrane there is a red spot at the Protein A control, 3. This indicates that the proper testing procedure was followed. A red spot at the antigen, 4, indicates that the sample added contained analyte antibody.

EXAMPLE 4

Assay for Antigen Detection

Referring to FIG. 7, Protein A, 3, is inoculated onto the membrane, 2, of an EY™ FASTCHEK™ device using the same procedure as described above in Example 1. Capture antibody, 7, typically a monoclonal capture antibody specific for one epitope of the analyte antigen, is immobilized onto another area of the solid phase using procedures known in the art. Analyte antigen, 8, is also immobilized onto the membrane.

After inoculation of the Protein A, the antigen, and the capture antibody, the immunoassay device is used to test for the presence of analyte antigen in human serum or plasma. Two drops of 1% BSA or other blocking buffer are added to the surface of the membrane and allowed to absorb into the membrane. Next, one drop of human serum or plasma is allowed to absorb into the membrane. This is followed by the addition of a monoclonal antibody cocktail, having a first colloidal-gold labelled antibody directed to an epitope of the analyte antigen and a second colloidal-gold labeled antibody specific for human IgG.

After the labeled monoclonal antibody cocktail absorbs through the membrane there is a red spot at the Protein A control, 3. This indicates that the proper testing procedure was followed. A red spot at the analyte antigen, 8, indicates that the monoclonal antibody specific for analyte antigen was properly functioning. A red spot at the capture antibody indicates that the sample tested contains analyte antibody.

What is claimed is:

1. An analytical device for use in immunoassays for the detection of a first analyte antibody in a liquid sample suspected of containing such antibody, comprising:

(a) a solid phase comprising a permeable membrane having a lower surface and an upper surface, (b) a first antigen, for which said first analyte antibody is specific, immobilized on a first area of said upper surface of said solid phase, (c) at least one non-antibody control substance selected from the group consisting of native Protein A, recombinant Protein A, native Protein G, and recombinant Protein G, wherein said control substance is immbolized on a second area of said upper surface of said solid phase, and (d) an absorbent body in liquid-transferring contact with the lower surface of said membrane.

2. The device of claim 1 wherein said first and second areas are in the shape of dots.

3. The device of claim 1 further comprising:

(d) a second antigen, for which a second analyte antibody is specific, immobilized on a third area of said upper surface of said solid phase.

4. The device of claim 3 wherein said first and third areas are in the shape of dots and said second area is in the shape of a bar horizontally disposed between said first and third areas.

5. The device of claim 1 wherein said first area is in the shape of a dot, and said second area is in the shape of an open circle surrounding said first area.

6. The device of claim 1 wherein said first area is in the shape of a first bar, and said second area is in the shape of a second bar transecting said first bar.

7. The device of claim 1 wherein said antigen is selected from the group consisting of Human Immunodeficiency Virus antigens, Hepatitis virus antigens, *Toxoplasmosis gondii*, Cytomegalovirus, *Helicobacter pylori*, and Rubella.

8. The device of claim 1 wherein said non-antibody control substance is native Protein A or recombinant Protein A.

9. An analytical device for use in immunoassays for the detection of an analyte antigen in a liquid sample suspected of containing such antigen, comprising:

(a) a solid phase comprising a permeable membrane having a lower surface and an upper surface, (b) capture antibody immbolized on a first area of said upper surface of said solid phase, said capture antibody being specific for said analyte antigen; and (c) at least one non-antibody control substance selected from the group consisting of native Protein A, recombinant Protein A, native Protein G, and recombinant Protein G, wherein said control substance is immobilized on a second area of said upper surface of said solid phase, and (d) an absorbent body in liquid-transferring contact with the lower surface of said membrane.

10. The device of claim 9 further comprising:

(d) analyte antigen immobilized on a third area of said upper surface of said solid phase.

11. The device of claim 9 wherein said non-antibody control substance is native Protein A or recombinant Protein A.

12. A method of determining whether functioning reagents have been added in proper sequence to an analytical device used for the detection of analyte antibody in a liquid sample suspected of containing such antibody, said device comprising:

(a) a solid phase, (b) an antigen, for which said analyte antibody is specific, immobilized on a first area of said solid phase, and (c) at least one non-antibody control substance selected from the group consisting of native Protein A, recombinant Protein A, native Protein G, and recombinant Protein G, wherein said control substance is immobilized on a second area of said solid phase;

said method comprising the steps of: (1) applying, to said first and second areas, said liquid sample and at least one labeled non-antibody substance selected from the group consisting of native Protein A, recombinant Protein A, native Protein G, and recombinant Protein G; and (2) examining said second area for the presence of said labeled substance wherein the presence of said labeled substance at said second area indicates that functioning reagents have been added to said analytical device in proper sequence.

13. The method of claim 12 wherein said solid phase comprises a permeable membrane having a lower surface and an upper surface, said first and second areas being located on the upper surface of said membrane.

14. The method of claim 13 wherein said device further comprises an absorbent body in liquid-transferring contact with the lower surface of said membrane.

15. The method of claim 12 wherein said antigen is selected from the group consisting of Human Immunodeficiency Virus antigens, Hepatitis virus antigens, *Toxoplasmosis gondii*, Cytomegalovirus, *Helicobacter pylori*, and Rubella.

16. The method of claim 12 wherein said non-antibody control substance is native Protein A or recombinant Protein A.

17. The method of claim 12 wherein said labeled non-antibody substance is native Protein A or recombinant Protein A.

18. The method of claim 12 wherein the label of said labeled non-antibody substance is a metal colloid.

19. The method of claim 12 wherein said liquid sample is added to said first and second areas prior to the addition of the labeled non-antibody substance.

20. An analytical method for the detection of analyte antibody in a liquid sample suspected of containing such antibody comprising:

(a) adding said sample to an analytical device, said device comprising:
  i. a solid phase,
  ii. an antigen, for which said analyte antibody is specific, immobilized on a first area of a solid phase; and,
  iii. at least one non-antibody control substance selected from the group consisting of native Protein A, recombinant Protein A, native Protein G, and recombinant Protein G, wherein said control substance is immobilized on a second area of a solid phase, (b) adding at least one labeled non-antibody substance selected from the group consisting of native Protein A, recombinant Protein A, native Protein G, and recombinant Protein G to said device, and (c) examining for the presence of said labeled substance at said first and second areas of said solid phase wherein the presence of labeled substance at said first and second areas indicates the presence of said analyte antibody in said liquid sample.

21. The method of claim 20 wherein said solid phase comprises a permeable membrane having a lower surface and an upper surface, said first and second areas being located on the upper surface of said membrane.

22. The method of claim 21 wherein said device further comprises an absorbent body in liquid-transferring contact with the lower surface of said membrane.

23. The method of claim 20 wherein said antigen is selected from the group consisting of Human Immunodeficiency Virus antigens, Hepatitis virus antigens, *Toxoplasmosis gondii*, Cytomegalovirus, *Helicobacter pylori*, and Rubella.

24. The method of claim 20 wherein said non-antibody control substance is native Protein A or recombinant Protein A.

25. The method of claim 20 wherein said labeled non-antibody substance is native Protein A or recombinant Protein A.

26. The method of claim 20 wherein the label of said labeled non-antibody substance is a metal colloid.

27. The method of claim 20 wherein said liquid sample is added to said analytical device prior to the addition of the labeled non-antibody substance.

28. An analytical method for the detection of analyte antigen in a liquid sample suspected of containing such antigen comprising:

(a) adding said sample and an antibody-conjugate cocktail, said cocktail comprising a first labeled antibody specific for immunoglobulin G and a second labeled antibody specific for said analyte antigen to an analytical device, said device comprising:
  i. a solid phase,
  ii. a capture antibody immobilized on a first area of said solid phase, said capture antibody being specific for said analyte antigen; and,
  iii. at least one non-antibody control substance selected from the group consisting of native Protein A, recombinant Protein A, native Protein G, and recombinant Protein G, wherein said control substance is immobilized on a second area of said solid phase; and (b) examining for the presence of said first labeled antibody at said first area of said solid phase, wherein the presence of said first labeled antibody at said first area indicates the presence of said analyte antigen in said liquid sample.

29. The method of claim 28 wherein said solid phase comprises a permeable membrane having a lower surface and an upper surface, said first and second areas being located on the upper surface of said membrane.

30. The method of claim 29 wherein said device further comprises an absorbent body in liquid-transferring contact with the lower surface of said membrane.

31. The method of claim 28 wherein said non-antibody control substance is native Protein A or recombinant Protein A.

32. The method of claim 28 wherein said capture antibody and said first labeled antibody are monoclonal antibodies, said capture antibody having specificity for a first epitope of said analyte antigen and said first labeled antibody having specificity for a second epitope of said analyte antigen.

33. The method of claim 28 wherein the label of said first and second labeled antibodies is a metal colloid.

\* \* \* \* \*